United States Patent
Young et al.

(10) Patent No.: US 10,348,419 B2
(45) Date of Patent: Jul. 9, 2019

(54) WIRELESS SENSOR WITH OPPOSITELY POSITIONED ANTENNA AND SENSING CIRCUITRY

(71) Applicant: RFMicron, Inc., Austin, TX (US)

(72) Inventors: Brian David Young, Austin, TX (US); Shahriar Rokhsaz, Austin, TX (US)

(73) Assignee: RFMicron, Inc., Austin, TX (US)

( * ) Notice: Subject to any disclaimer, the term of this patent is extended or adjusted under 35 U.S.C. 154(b) by 119 days.

(21) Appl. No.: 15/430,899

(22) Filed: Feb. 13, 2017

(65) Prior Publication Data

US 2017/0162931 A1 Jun. 8, 2017

Related U.S. Application Data

(63) Continuation-in-part of application No. 14/879,088, filed on Oct. 8, 2015, now Pat. No. 9,582,981.

(Continued)

(51) Int. Cl.

| | |
|---|---|
| *H04B 17/00* | (2015.01) |
| *H04B 17/10* | (2015.01) |
| *H04B 17/20* | (2015.01) |
| *A61F 13/42* | (2006.01) |
| *G01N 27/04* | (2006.01) |
| *G01N 27/22* | (2006.01) |
| *G08B 21/20* | (2006.01) |

(Continued)

(52) U.S. Cl.
CPC .............. *H04B 17/00* (2013.01); *H04B 17/10* (2015.01); *H04B 17/20* (2015.01); *A61F 13/42* (2013.01); *A61F 2013/424* (2013.01); *G01N 27/048* (2013.01); *G01N 27/225* (2013.01); *G01N 2035/00881* (2013.01); *G06K 19/0717* (2013.01); *G08B 21/20* (2013.01)

(58) Field of Classification Search
CPC ...... H04B 17/00; H04B 17/10; H04B 17/101; H04B 17/15; H04B 17/20; H04B 17/23; H04B 17/25; H04B 17/27; H04B 17/29; H04B 17/30; H04B 17/318; H04B 17/336; H04B 17/345; G08B 21/00; G01N 1/00; A61B 5/6808; A61F 13/42
See application file for complete search history.

(56) References Cited

U.S. PATENT DOCUMENTS

| | | | |
|---|---|---|---|
| 7,411,390 B2 * | 8/2008 | Goldfine .................. | G01V 3/15 324/202 |
| 8,432,322 B2 * | 4/2013 | Amm ..................... | H01Q 1/243 324/658 |

(Continued)

*Primary Examiner* — Van T Trieu
(74) *Attorney, Agent, or Firm* — Garlick & Markison; Timothy W. Markison

(57) ABSTRACT

A wireless sensor includes a substrate, an antenna, a sensing element, a transmission line, and a sensing integrated circuit (IC). The sensing element is positioned on one end of the substrate and the antenna is positioned on an opposite end of the substrate. The sensing IC is coupled to the sensing element and to the antenna via the transmission line. The sensing IC is operable to receive a sensed condition of the item from the sensing element. The sensing IC is further operable to determine an input impedance of the wireless sensor based on the sensed condition and convert it into a digital value that is representative of the condition of the item. The sensing IC is further operable to output, via the antenna, the digital value or a representation of the condition of the item.

14 Claims, 6 Drawing Sheets

Related U.S. Application Data

(60) Provisional application No. 62/295,023, filed on Feb. 13, 2016, provisional application No. 62/061,257, filed on Oct. 8, 2014, provisional application No. 62/079,369, filed on Nov. 13, 2014, provisional application No. 62/147,890, filed on Apr. 15, 2015, provisional application No. 62/195,038, filed on Jul. 21, 2015.

(51) Int. Cl.
  *G06K 19/07* (2006.01)
  *G01N 35/00* (2006.01)

(56) References Cited

U.S. PATENT DOCUMENTS

| | | | | |
|---|---|---|---|---|
| 2004/0021461 A1* | 2/2004 | Goldfine | ............... | G01V 3/15 324/243 |
| 2009/0143028 A1* | 6/2009 | Kim | ............... | H04B 17/27 455/90.2 |
| 2011/0012793 A1* | 1/2011 | Amm | ............... | H01Q 1/243 343/702 |
| 2017/0356812 A1* | 12/2017 | Madden | ............... | G06F 3/044 |

* cited by examiner wireless communication system 10

US 10,348,419 B2

WIRELESS SENSOR WITH OPPOSITELY POSITIONED ANTENNA AND SENSING CIRCUITRY

CROSS REFERENCE TO RELATED PATENTS

The present U.S. Utility Patent Application claims priority pursuant to 35 U.S.C. § 119(e) to U.S. Provisional Application No. 62/295,023, entitled "RFID Sensors with Distally Disposed Sensing Integrated Circuit", filed Feb. 13, 2016, which is hereby incorporated herein by reference in its entirety and made part of the present U.S. Utility Patent Application for all purposes.

The present U.S. Utility Patent Application further claims priority pursuant to 35 U.S.C. § 120 as a continuation-in-part of U.S. Utility application No. 14/879,088, entitled "Radio Frequency Identification (RFID) Moisture Tag(s) And Sensors With Extended Sensing Via Capillaries", filed Oct. 8, 2015, issuing as U.S. Pat. No. 9,582,981 on Feb. 28, 2017, which claims priority pursuant to 35 U.S.C. § 119(e) to U.S. Provisional Application No. 62/061,257, entitled "Radio Frequency Identification (RFID) Moisture Tags and Sensors", filed Oct. 8, 2014, U.S. Provisional Application No. 62/079,369, entitled "Radio Frequency Identification (RFID) Moisture Tags and Sensors", filed Nov. 13, 2014, U.S. Provisional Application No. 62/147,890, entitled "Radio Frequency Identification (RFID) Moisture Tags and Sensors with Extended Sensing", filed Apr. 15, 2015, and U.S. Provisional Application No. 62/195,038, entitled "RFID Moisture Tags and Sensors with Extended Sensing via Capillaries", filed Jul. 21, 2015.

STATEMENT REGARDING FEDERALLY SPONSORED RESEARCH OR DEVELOPMENT

Not Applicable

INCORPORATION-BY-REFERENCE OF MATERIAL SUBMITTED ON A COMPACT DISC

Not Applicable

BACKGROUND OF THE INVENTION

Technical Field of the Invention

This invention relates generally to wireless communications and more particularly to wireless sensors and applications thereof.

Description of Related Art

Wireless communication systems are known to include wireless transceivers that communication directly and/or over a wireless communication infrastructure. In direct wireless communications, a first wireless transceiver includes baseband processing circuitry and a transmitter to convert data into a wireless signal (e.g., radio frequency (RF), infrared (IR), ultrasound, near field communication (NFC), etc.). Via the transmitter, the first wireless transceiver transmits the wireless signal. When a second wireless transceiver is in range (e.g., is close enough to the first wireless transceiver to receive the wireless signal at a sufficient power level), it receives the wireless signal via a receiver and converts the signal into meaningful information (e.g., voice, data, video, audio, text, etc.) via baseband processing circuitry. The second wireless transceiver may wirelessly communicate back to the first wireless transceiver in a similar manner.

Examples of direct wireless communication (or point-to-point communication) include walkie-talkies, Bluetooth, ZigBee, Radio Frequency Identification (RFID), etc. As a more specific example, when the direct wireless communication is in accordance with RFID, the first wireless transceiver may be an RFID reader and the second wireless transceiver may be an RFID tag.

For wireless communication via a wireless communication infrastructure, a first wireless communication device transmits a wireless signal to a base station or access point, which conveys the signal to a wide area network (WAN) and/or to a local area network (LAN). The signal traverses the WAN and/or LAN to a second base station or access point that is connected to a second wireless communication device. The second base station or access point sends the signal to the second wireless communication device. Examples of wireless communication via an infrastructure include cellular telephone, IEEE 802.11, public safety systems, etc.

In many situations, direct wireless communication is used to gather information that is then communicated to a computer. For example, an RFID reader gathers information from RFID tags via direct wireless communication. At some later point in time (or substantially concurrently), the RFID reader downloads the gathered information to a computer via a direct wireless communication or via a wireless communication infrastructure.

In many RFID systems, the RFID tag is a passive component. As such, the RFID tag has to generate one or more supply voltages from the RF signals transmitted by the RFID reader. Accordingly, a passive RFID tag includes a power supply circuit that converts the RF signal (e.g., a continuous wave AC signal) into a DC power supply voltage.

The power supply circuit includes one or more diodes and one or more capacitors. The diode(s) function to rectify the AC signal and the capacitor(s) filter the rectified signal to produce the DC power supply voltage, which powers the circuitry of the RFID tag.

Once powered, the RFID tag receives a command from the RFID reader to perform a specific function. For example, if the RFID tag is attached to a particular item, the RFID tag stores a serial number, or some other identifier, for the item. In response to the command, the RFID tag retrieves the stored serial number and, using back-scattering, the RFID tag transmits the retrieved serial number to the RFID reader.

For instance, in automobiles, wireless tire pressure monitoring sensors are used to provide tire pressure information to an automobile's computer. The sensors may indirectly or directly sense tire pressure. For example, indirect sensing calculates tire pressure from measured revolutions of the tire via the sensor. As another example, direct sensing measures the tire pressure from inside the tire. Direct sensing provides a more accurate measure of tire pressure than indirect sensing, but does so at a cost. In particular, direct wireless sensors include a battery and micro-electromechanical semiconductor (MEMS) circuitry to sense the tire pressure.

BRIEF DESCRIPTION OF THE SEVERAL VIEWS OF THE DRAWING(S)

DETAILED DESCRIPTION OF THE INVENTION

Figure 1:
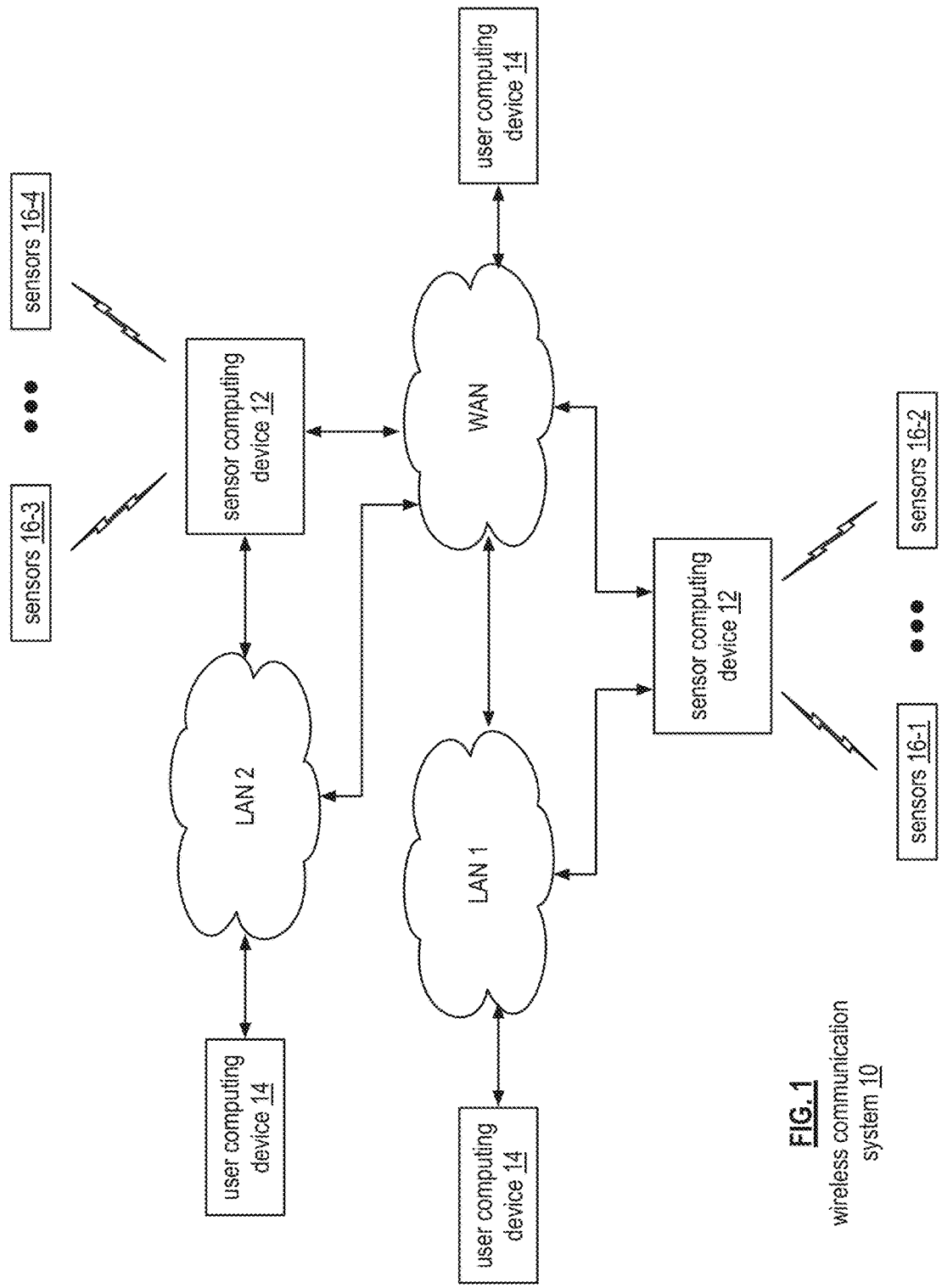
FIG. 1 is a schematic block diagram of an embodiment of a communication system in accordance with the present invention.

FIG. 1 is a schematic block diagram of an embodiment of a communication system 10 that includes a plurality of sensor computing device 12, a plurality of user computing devices 14, a plurality of wireless sensors 16-1 through 16-4 (e.g., passive or active), one or more wide area networks (WAN), and one or more local area networks (LAN). The wireless sensors 16-1 through 16-4, when activated, sense one or more of a variety of conditions. For example, one wireless sensor senses for the presence, absence, and/or amount of moisture in a given location (e.g., in a room, in a manufactured item or component thereof (e.g., a vehicle), in a bed, in a diaper, etc.). As another example, a wireless sensor senses pressure on and/or in a particular item (e.g., on a seat, on a bed, in a tire, etc.).

As yet another example, a wireless sensor senses temperature within a space and/or of an item (e.g., surface temperature of the item, in a confined space such as a room or a box, etc.). As a further example, a wireless sensor senses humidity within a space (e.g., a room, a closet, a box, a container, etc.). As a still further example, a wireless sensor senses the presence and/or percentages of a gas within a space (e.g., carbon monoxide in a car, carbon monoxide in a room, gas within a food container, etc.). As an even further example, a wireless sensor senses the presence and/or percentages of light within a space. As yet a further example, a wireless sensor senses the presence, percentages, and/or properties of one or more liquids in a solution. In one more example, a wireless sensor senses location proximity of one item to another and/or the proximity of the wireless sensor to an item (e.g., proximity to a metal object, etc.).

In general, the sensor computing devices 12 function to collect the sensed data from the wireless sensors and process the sensed data. For example, a wireless sensor generates a coded value representative of a sensed condition (e.g., amount of moisture). A sensor computing device 12 receives the coded value and processes it to determine an accurate measure of the sensed condition (e.g., a value corresponding to the amount of moisture such as 0% saturated, 50% saturated, 100% saturated, etc.).

The user computing devices 14 communicate with one or more of the sensor computing devices 12 to gather the accurate measures of sensed conditions for further processing. For example, assume that the wireless communication system is used by a manufacturing company that has multiple locations for assembly of its products. In particular, LAN 1 is at a first location where a first set of components of products are processed and the LAN 2 is at a second location where second components of the products and final assembly of the products occur. Further assume that the corporate headquarters of the company is at a third location, where it communicates with the first and second locations via the WAN and LANs.

In this example, the sensor computing device 12 coupled to LAN 1 collects and processes data regarding the first set of components as sensed by wireless sensors 16-1 and 16-2. The sensor computing device 12 is able to communicate this data to the user computing device 14 coupled to the LAN 1 and/or to the computing device 14 at corporate headquarters via the WAN. Similarly, the sensor computing device 12 coupled to LAN 2 collects and processes data regarding the second set of components and final assembly as sensed by wireless sensors 16-3 and 16-4. This sensor computing device 12 is able to communicate this data to the user computing device 14 coupled to the LAN 2 and/or to the computing device 14 at corporate headquarters via the WAN. In such a system, real time monitor is available locally (e.g., via the LAN) and is further available non-locally (e.g., via the WAN). Note that any of the user computing devices 14 may receive data from the any of the sensor computing devices 12 via a combination of LANs and the WAN.

Figure 2:
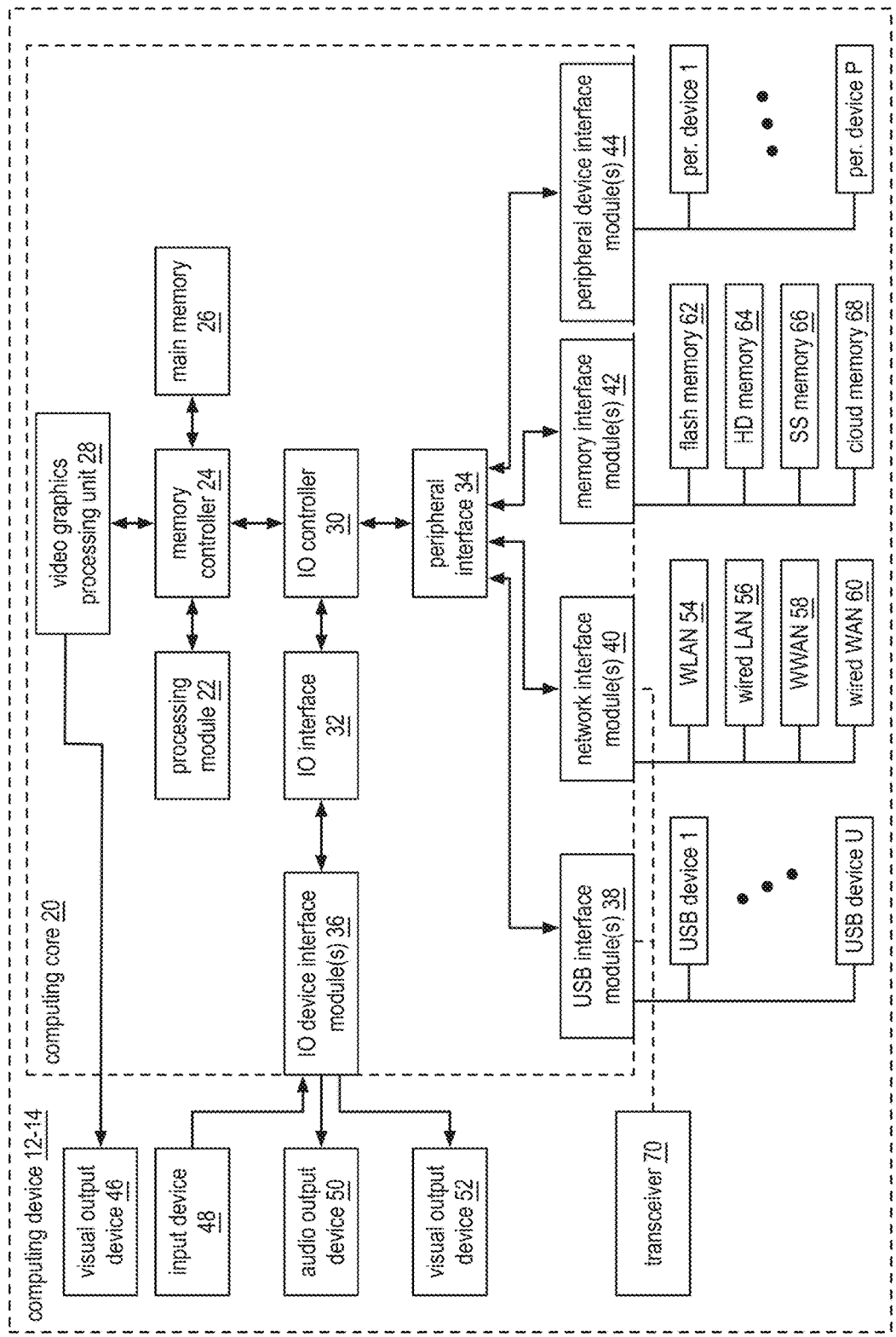
FIG. 2 is a schematic block diagram of an embodiment of a computing device in accordance with the present invention.

FIG. 2 is a schematic block diagram of an embodiment of a computing device 12 and/or 14 that includes a computing core 20, one or more input devices 48 (e.g., keypad, keyboard, touchscreen, voice to text, etc.), one or more audio output devices 50 (e.g., speaker(s), headphone jack, etc.), one or more visual output devices 46 (e.g., video graphics display, touchscreen, etc.), one or more universal serial bus (USB) devices, one or more networking devices (e.g., a wireless local area network (WLAN) device 54, a wired LAN device 56, a wireless wide area network (WWAN) device 58 (e.g., a cellular telephone transceiver, a wireless data network transceiver, etc.), and/or a wired WAN device 60), one or more memory devices (e.g., a flash memory device 62, one or more hard drives 64, one or more solid state (SS) memory devices 66, and/or cloud memory 96), one or more peripheral devices, and/or a transceiver 70.

The computing core 20 includes a video graphics processing unit 28, one or more processing modules 22, a memory controller 24, main memory 26 (e.g., RAM), one or more input/output (I/O) device interface module 36, an input/output (I/O) interface 32, an input/output (I/O) controller 30, a peripheral interface 34, one or more USB interface modules 38, one or more network interface modules 40, one or more memory interface modules 42, and/or one or more peripheral device interface modules 44. Each of the interface modules 36-44 includes a combination of hardware (e.g., connectors, wiring, etc.) and operational instructions stored on memory (e.g., driver software) that is executed by the processing module 22 and/or a processing circuit within the respective interface module. Each of the interface modules couples to one or more components of the computing device 12-14. For example, one of the IO device interface modules 36 couples to an audio output device 50. As another example, one of the memory interface modules 42 couples to flash memory 62 and another one of the memory interface modules 42 couples to cloud memory 68 (e.g., an on-line storage system and/or on-line backup system).

The transceiver 70 is coupled to the computing core 20 via a USB interface module 38, a network interface module 40, a peripheral device interface module 44, or a dedicated interface module (not shown). Regardless of how the transceiver 70 is coupled to the computing core, it functions to communication with the passive wireless sensors.

Figure 3:
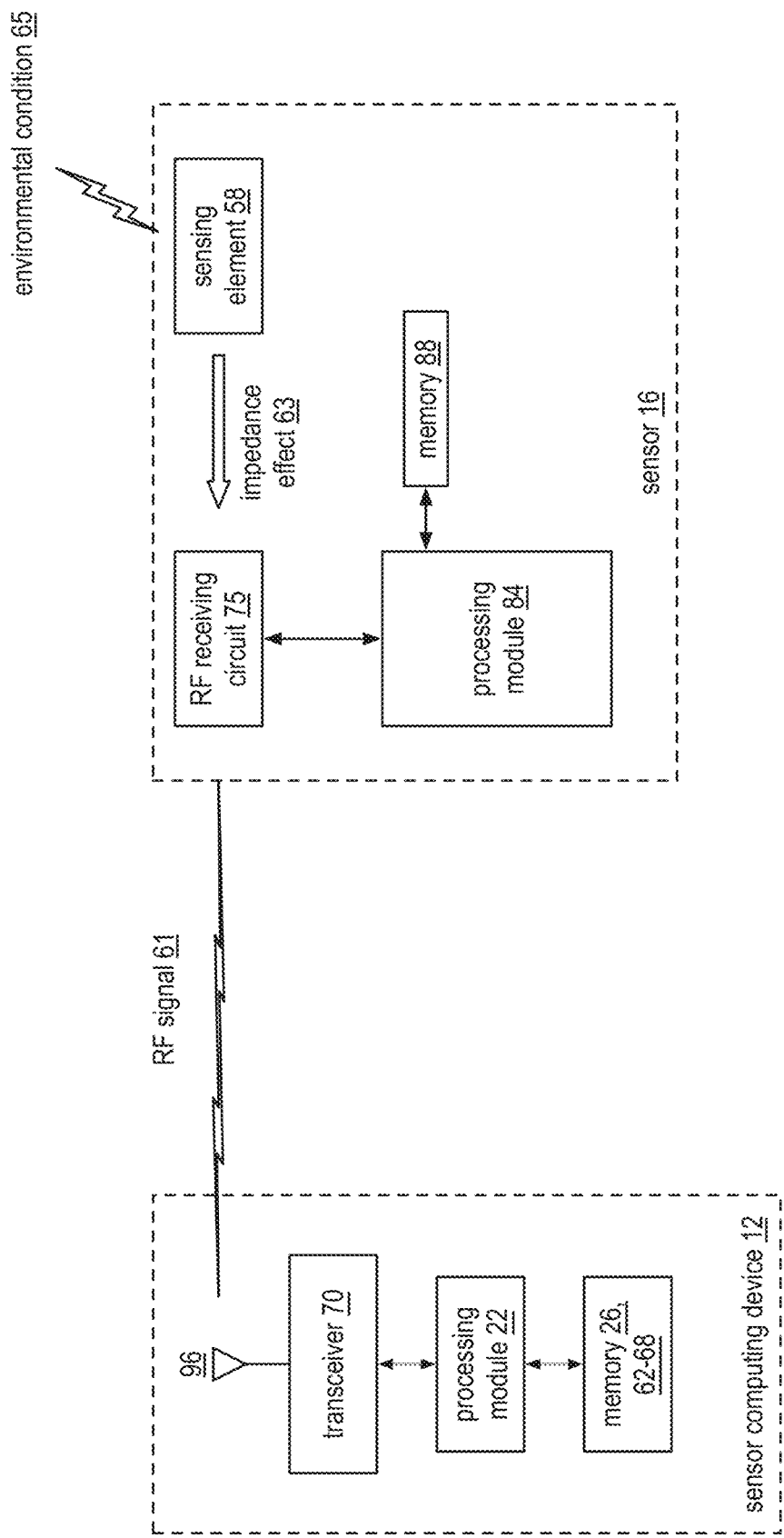
FIG. 3 is a schematic block diagram of an example of a sensor computing device communicating with a wireless sensor in accordance with the present invention.

FIG. 3 is a schematic block diagram of an example of a sensor computing device 12 communicating with a wireless sensor 16 (e.g., any one of 16-1 through 16-4). The sensor computing device 12 is illustrated in a simplified manner; as such, it shown to include the transceiver 70, an antenna 96, the processing module 22, and the memory (e.g., one or more 26 and 62-68). The wireless sensor 16 includes an RF front end 75 (e.g., receiver section, transmitter section, antenna, and/or a tuning circuit), a processing module 84, and memory 88.

In an example, the sensing element 58 of the wireless sensor 16 senses an environmental condition 65 of an object or item. The environment condition 65 includes, but is not limited to, one or more of moisture, temperature, pressure, humidity, altitude, sonic wave (e.g., sound), human contact, surface conditions, tracking, location, etc. The object or item includes one or more of, but is not limited to, a box, a personal item (e.g., clothes, diapers, etc.), a pet, an automobile component, an article of manufacture, an item in transit, blood, liquid, gas, etc. The sensing element 58 senses the environmental condition (e.g., moisture) and, as a result of the sensed condition, the sensing element 58 affects 63 an operational parameter (e.g., input impedance, quality factor, frequency, etc.) of an RF front end 75.

As a specific example, the sensing element 58, as a result of the sensed environmental condition 65, affects the input impedance of the antenna structure and/or of the tuning circuit (e.g., a tank circuit that includes one or more capacitors and one or inductors having a resonant frequency corresponding to the carrier frequency of the RF signal) of the RF front end 75. In response to the impedance change, the processing module 84 adjusts the resonant frequency of the tuning circuit to compensate for the change in input impedance caused by the sensed environmental condition. The amount of adjustment is reflective of the level of the environmental condition (e.g., a little change corresponds to a little moisture; a large change corresponds to a large amount of moisture). The processing module 84 generates a coded digital value to represent the amount of adjustment and conveys the coded value to the sensor computing device 12 via the transmitter section and the antenna of the RF front end 75 using back-scattering.

In addition to processing the sensed environmental condition, the processing module 84 processes a power level adjustment. For example, a power detection circuit of the wireless sensor 16 detects a power level of a received RF signal. In one embodiment, the processing module interprets the power level and communicates with the sensor computing device 12 to adjust the power level of the RF signal transmitted by the computing device 12 to a desired level (e.g., optimal for accuracy in detecting the environmental condition). In another embodiment, the processing module 84 includes the received power level data with the environmental sensed data it sends to the sensor computing device 12 so that the computing device can factor the power level into the determination of the environmental condition.

Figure 4:
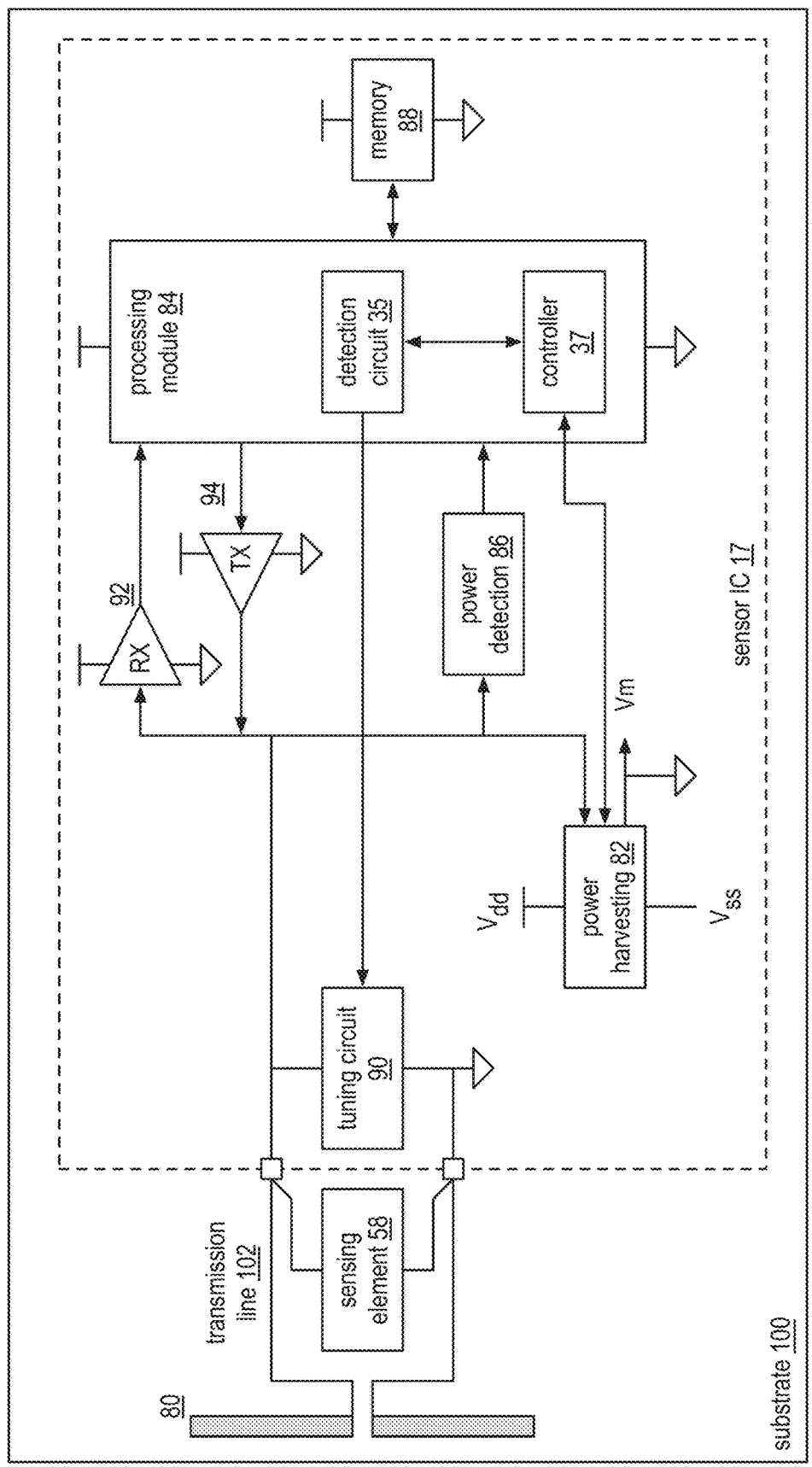
FIG. 4 is a schematic block diagram of an embodiment of a wireless sensor in accordance with the present invention.

FIG. 4 is a schematic block diagram of an embodiment of a wireless sensor that includes a substrate 100, an antenna 80 (e.g. dipole, monopole, spiral, meandering trace, etc.), a transmission line 102, the sensing element 58, and a sensor integrated circuit (IC) 17. The sensor IC 17 includes the processing module 84, the memory 88, a transmitter section 94, a receiver section 92, a power harvesting circuit 82, a power detection circuit 86, and a tuning circuit 90. The processing module 84 is configured to include a controller 37 and a detection circuit 35.

In an example of operation, the wireless sensor is associated with an item and an identifier of the item is stored in the memory 88. The item is one or more of a gas, liquid, solid, composition, article or manufacture, a bodily fluid (e.g., urine, blood, saliva, etc.), an animal, and an inanimate object (e.g., a wall, a chair, an automobile part, etc.). The wireless sensor may be directing attached to the item or it may sense the item through the item's container (e.g., sensing temperature and/or level of blood in a bag).

In a specific example, the item and/or the container have properties that interfere with RF communications. In particular, the item and/or container is electrically conductive, which substantially attenuates RF signals in its immediately surrounding area. As such, if the antenna 80 were place over the item and/or the container, the ability for the sensor computing device and the wireless sensor to communicate via RF signals would be severely compromised and, in many instances, prevented.

To substantially overcome this issue, the antenna 80 is placed at one end of the substrate 100 (e.g., a flexible printed circuit board and/or a printed plastic membrane) and the sensing element 58 is placed at the other end. When the wireless sensor is place on the item or container, the end with the sensing element 58 is placed proximal to the item to sense conditions of the item and the antenna end of the wireless sensor is positioned away from the item and/or container to substantially avoid RF signal interference of the item and/or container.

The sensing element 58 may be one of a variety of sensors sensing one or more of a variety of conditions. For example, the sensing element measures the temperatures of fluids, such as blood bags. As another example, the sensing element senses moisture or temperature inside of a container that functions like an RF shield (e.g., metal, cavities in automobile body parts, etc.). As yet another example, the sensing element senses moisture or temperature at a location with overlaying metal or electronics that block the RF signal (e.g., the floor of a car, a metallic panel, a speaker, an audio amplifier, other electronics, a crib, a mattress pad, etc.). As a further example, the sensing element senses moisture or temperature at location that is physically too small to fit an antenna but can accommodate the tip of the tail.

For the sensing computing device 12 to communicate with the wireless sensor 16, the sensor 16 first generates a power supply voltage (or multiple power supply voltages) from an RF (radio frequency) signal transmitted by the sensing computing device 12. For example, the RF signal 61 is a continuous wave signal and uses amplitude shift keying (ASK) or other amplitude-based modulation scheme to convey data.

The power harvesting circuit 82 receives the RF signal 61 via the antenna 80 and converts it into one or more supply voltages (Vs). The supply voltage(s) power the other components (e.g., 84, 86, 92 and 94) so that they perform their specific tasks. For instance, the receiver 92 is operable to convert an inbound message received from the sensing computing device into a baseband signal that it provides to the processing module 84. The processing module 84 processes the baseband signal and, when appropriate, generates a response that is subsequently transmitted via the antenna 80 by the transmitter 94. For example, the inbound message instructs the wireless sensor to provide a respond with a pressure measurement and the stored ID of the item.

To obtain a measurement of a condition of the item, the sensing circuit 58 senses the item. For instance, the sensing circuit 58 is producing a change to one or more of capacitance, inductance, resistance, resonant frequency, and antenna loading of the wireless sensor as an indication of the condition of the item. For example, when the sensing element 58 is sensing for moisture, as the presence of moisture increases, the impedance of the sensing element will decrease affecting one or more of the capacitance, inductance, resistance, and antenna loading of the wireless sensor. As another example, when the sensing element 58 is sensing for gases, its resistance changes in the presence of gases such as CO, $CO_2$, $NO_x$, $H_2S$, $O_2$, and Cb. As a further example, when the sensing element is sensing for proximity, movement, or pressure, the sensing element experiences inductive changes created by eddy currents on nearby metal surfaces.

The changing electrical characteristics of the sensing circuit 58 causes a change in an RF characteristic of the RF front end 75, which includes the antenna 80, the tuning circuit 90, and the sensing circuit 58. Note that an RF characteristic includes an impedance (e.g., an input impedance) at a frequency (e.g., carrier frequency of the RF signal), a resonant frequency (e.g., of the turning circuit and/or antenna), a quality factor (e.g., of the antenna), and/or a gain. As a specific example, the resonant frequency has changed from a desired resonant frequency (e.g., matching the carrier frequency of the RF signal) as result of the sensed condition.

The processing module 84 detects, via the detection circuit 35, a variance of the one or more RF characteristics from a desired value (e.g., the resonant frequency changes from a desired frequency that corresponds to the carrier frequency of the RF signal). When the processing module detects the variance, it adjusts the tuning circuit to substantially re-establish the desired value of the one or more RF characteristics. For example, the tuning circuit 90 includes an inductor and a capacitor, at least one of which is adjusted to change the resonant frequency back to the desired value.

The processing module 84 determines the amount of adjusting of the tuning circuit 90 and converts the amount of adjusting into a digital value. The digital value is representative of the sensed condition of the item by the sensing circuit 58. For example, the digital value represents a change in the condition with respect to a reference condition (increasing temperature, increasing moisture level, etc.). As another example, the digital represents a measure of the condition (e.g., a temperature, a moisture level, a pressure level, etc.).

The processing module 84 generates a message regarding the adjusting of the tuning circuit (e.g., the message includes the digital value or an actual measurement if the processing module performs a digital value to measurement conversion function). The transmitter 94 transmits the message to the sensing computing device 12 via the antenna 80 or another antenna (not shown).

Before the processing module 84 processes the sensed condition, it may perform a power level adjustment. For example, the power detection circuit 86 detects a power level of the received RF signal. In one embodiment, the processing module interprets the power level and communicates with the sensing computing device 12 to adjust the power level of the RF signal to a desired level (e.g., optimal for accuracy in detecting the environmental condition). In another embodiment, the processing module includes the received power level data with the digital it sends to the sensing computing device 12 so that the computing device 12 can factor the power level into the determination of the extent of the condition.

The processing module 84 may be further operable to perform a calibration function when the condition in which the sensor is known (e.g., in a room at a certain altitude, in a calibration chamber having a set pressure, at a known temperature, etc.). For example, the processing module 84 receives a calibration request from a sensing computing device. In response, the processing module adjusts the tuning circuit to establish the desired value of the RF characteristic(s) (e.g., resonant frequency, input impedance, quality factor, gain, etc.). The processing module then records a level of the adjusting of the tuning circuit to represent a calibration digital value of the wireless sensor (e.g., records a digital value). The processing module may communicate the calibration value to the sensing computing device 12 as part of the calibration process or send it along with the digital value of a condition measurement.

Figure 5:
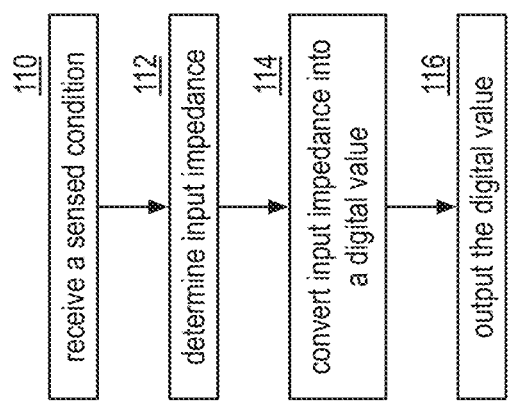
FIG. 5 is a logic diagram of an example of determining a digital value by a wireless sensor in accordance with the present invention.

FIG. 5 is a logic diagram of an example of determining a digital value by a wireless sensor that begins at step 110 where the sensor IC of the wireless sensor receives a sensed condition of the item from the sensing element (e.g., a change in an RF characteristic of the RF front end). The method continues at step 112 where the sensor IC determines an input impedance of the wireless sensor based on the sensed condition. For example, the sensor IC determines a change in the resonant frequency of the RF front end, which corresponds to a change in the input impedance of the RF front end of the wireless sensor.

The method continues at step 114 where the sensor IC converts the input impedance into a digital value that is representative of the condition of the item. For example, the sensor IC adjusts the tuning circuit such that the resonant frequency of the RF front end substantially matches the frequency of the received RF signal. The adjustment amount of the tuning circuit is determined and converted into the digital value. The method continues at step 116 where the sensor IC outputs, via the antenna, the digital value or a representation of the condition of the item (e.g., the sensor IC interprets the digital value to determine a measure of the condition of the item).

Figure 6:
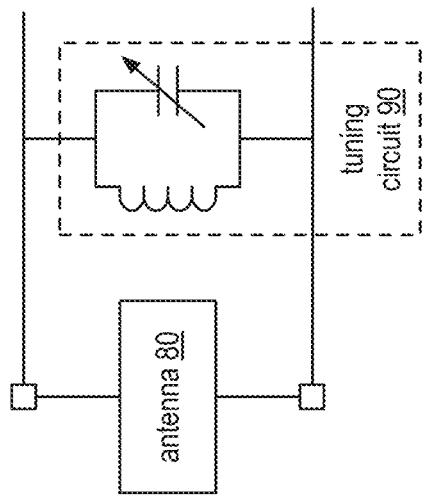
FIG. 6 is a schematic block diagram of an embodiment of an antenna and tuning circuit of a wireless sensor in accordance with the present invention.

FIG. 6 is a schematic block diagram of an embodiment of an antenna 80 and tuning circuit 90 of a wireless sensor 16. The tuning circuit includes an inductor and a variable capacitor (e.g., a varactor, a switchable capacitor bank, etc.). The capacitor is adjusted to retune the RF front end's resonant frequency to substantially match the carrier frequency of the received RF signal as the sensing element changes an RF characteristic of the RF front end due to condition changes of the item (e.g., temperature; moisture; pressure; concentration level of the item; and presence or absence detection of the item).

Figure 7:
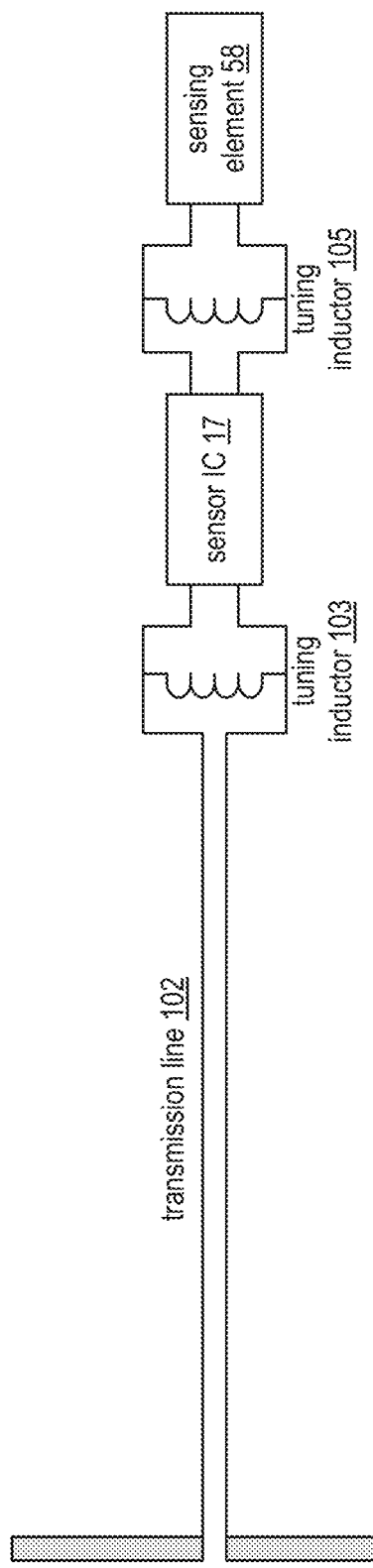
FIG. 7 is a schematic block diagram of another embodiment of a wireless sensor in accordance with the present invention.

FIG. 7 is a schematic block diagram of another embodiment of a wireless sensor 16 that includes the antenna 80, the transmission line 102, a first tuning inductor 103, the sensor IC 17, a second tuning inductor 105, and the sensing element 58. The tuning inductors 103 and 105 form a transformer that assistance in impedance matching of the sensor IC 17 and the transmission line 102. As is shown, the antenna 80 is distally located from the sensing element 58 and the sensor IC 17.

Figure 8:
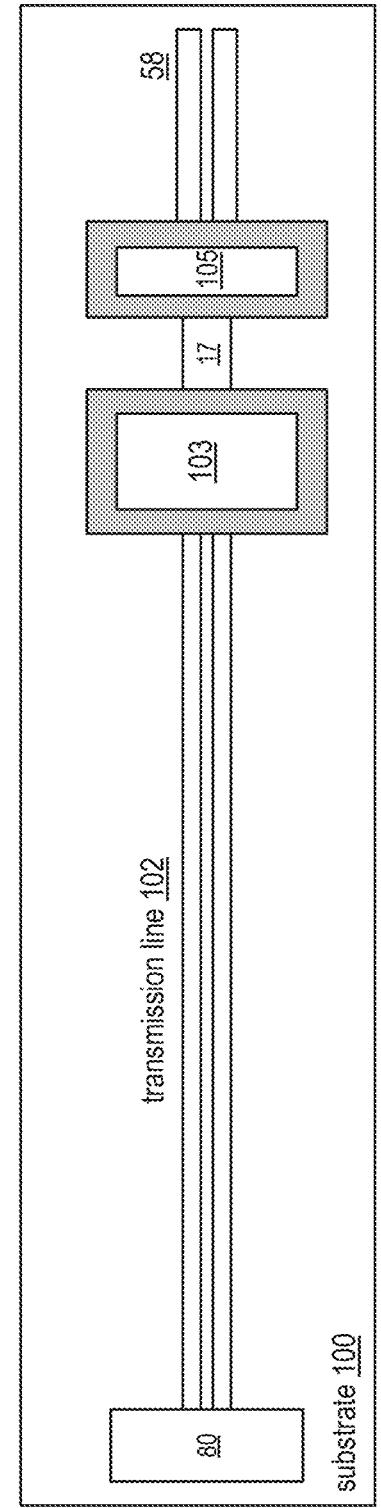
FIG. 8 is a schematic block diagram of another embodiment of a wireless sensor in accordance with the present invention.

FIG. 8 is a schematic block diagram of another embodiment of a wireless sensor 16 that includes the substrate 100, the antenna 80, the transmission line 102, a first tuning inductor 103, the sensor IC 17, a second tuning inductor 105, and the sensing element 58. In this embodiment, the sensing element 58 includes two parallel metallic traces (e.g., any conductive metal or electrically conductive material) that form a capacitor. Each of the metallic traces of the sensing element has a length and thickness and are separated by a spacing. The transmission line 102 includes metallic traces that also have a length, a thickness and are separated by a spacing. Variations in the length, thickness, and/or spacing of the metallic traces of the sensing element and/or of the transmission line 102 effect impedances of the wireless sensor.

The antenna 80 is shown as a dipole antenna with a ½ wavelength length, where each antenna leg as a ¼ wavelength length. In an embodiment, the length of the transmission line is equal to or greater than ¼ wavelength length such that the antenna 80 is far enough removed from the sensing element to minimize the RF communication adverse effects of the item being sensed. Note that the antenna 80 may be rotated 90 degrees from the orientation shown in the figure. Further note that the transmission line 102 may have a different shape than a straight line. Still further note that the antenna impedance at RF and the impedance of the transmission line are substantially equal and may be 77 Ohms.

In an embodiment, the antenna is disposed on single-layer PCB (e.g., substrate 100) with dimensions of 360.84 mm×146.92 mm. The board material is a 5 mil Kapton (in other embodiments, any material approximating PET in terms of dielectric constant would be suitable). The copper (Cu) weight is 0.5 oz with a gold flash finish, with a white silkscreen and no coverlay/soldermask. In another embodiment that is suitable for volume manufacturing, the construction would be 9 μm aluminum on 50 μm PET with or without a thin (=12 μm) PET cover layer.

The inlay construction of the wireless sensor is 9 μm aluminum on 50 μm PET with a thin coverlay. The antenna requires 2 mm of spacer consisting of 2 layers of, for example, 3M VHB 5952. The spacer is backed by thin PET with metallization to form a consistent ground plane. Adhesive then adheres the sensor IC to a metal surface. In some embodiments where the application of the sensor IC is expected to be onto inconsistent surfaces in terms of planarity and surface treatment, including thick and rough non-metallic coatings [sound deadeners], the presence of the backside plane integrated into the construction is critical.

The spacer may continue under the tail, but it is not required and thus enables flexibility and ease of installation. Since the slot line gap is only 90 the fields are tightly constrained and very tolerant of installation variables. For example, the tail can be laid or taped directly down to metal.

The transformer at the end of the tail cannot sit directly on metal because the presence of the metal detunes the transformer. A 2 mm spacer is placed between the transformer and a metal surface. A spacer is not required if the transformer is placed on any thick dielectric surface. In any configuration, dielectric materials can be placed directly on top of the transformer.

It is noted that terminologies as may be used herein such as bit stream, stream, signal sequence, etc. (or their equivalents) have been used interchangeably to describe digital information whose content corresponds to any of a number of desired types (e.g., data, video, speech, audio, etc. any of which may generally be referred to as 'data').

As may be used herein, the terms "substantially" and "approximately" provides an industry-accepted tolerance for its corresponding term and/or relativity between items. Such an industry-accepted tolerance ranges from less than one percent to fifty percent and corresponds to, but is not limited to, component values, integrated circuit process variations, temperature variations, rise and fall times, and/or thermal noise. Such relativity between items ranges from a difference of a few percent to magnitude differences. As may also be used herein, the term(s) "configured to", "operably coupled to", "coupled to", and/or "coupling" includes direct coupling between items and/or indirect coupling between items via an intervening item (e.g., an item includes, but is not limited to, a component, an element, a circuit, and/or a module) where, for an example of indirect coupling, the intervening item does not modify the information of a signal but may adjust its current level, voltage level, and/or power level. As may further be used herein, inferred coupling (i.e., where one element is coupled to another element by inference) includes direct and indirect coupling between two items in the same manner as "coupled to". As may even further be used herein, the term "configured to", "operable to", "coupled to", or "operably coupled to" indicates that an item includes one or more of power connections, input(s), output(s), etc., to perform, when activated, one or more its corresponding functions and may further include inferred coupling to one or more other items. As may still further be used herein, the term "associated with", includes direct and/or indirect coupling of separate items and/or one item being embedded within another item.

As may be used herein, the term "compares favorably", indicates that a comparison between two or more items, signals, etc., provides a desired relationship. For example, when the desired relationship is that signal 1 has a greater magnitude than signal 2, a favorable comparison may be achieved when the magnitude of signal 1 is greater than that of signal 2 or when the magnitude of signal 2 is less than that of signal 1. As may be used herein, the term "compares unfavorably", indicates that a comparison between two or more items, signals, etc., fails to provide the desired relationship.

As may also be used herein, the terms "processing module", "processing circuit", "processor", and/or "processing unit" may be a single processing device or a plurality of processing devices. Such a processing device may be a microprocessor, micro-controller, digital signal processor, microcomputer, central processing unit, field programmable gate array, programmable logic device, state machine, logic circuitry, analog circuitry, digital circuitry, and/or any device that manipulates signals (analog and/or digital) based on hard coding of the circuitry and/or operational instructions. The processing module, module, processing circuit, and/or processing unit may be, or further include, memory and/or an integrated memory element, which may be a single memory device, a plurality of memory devices, and/or embedded circuitry of another processing module, module, processing circuit, and/or processing unit. Such a memory device may be a read-only memory, random access memory, volatile memory, non-volatile memory, static memory, dynamic memory, flash memory, cache memory, and/or any device that stores digital information. Note that if the processing module, module, processing circuit, and/or processing unit includes more than one processing device, the processing devices may be centrally located (e.g., directly coupled together via a wired and/or wireless bus structure) or may be distributedly located (e.g., cloud computing via indirect coupling via a local area network and/or a wide area network). Further note that if the processing module, module, processing circuit, and/or processing unit implements one or more of its functions via a state machine, analog circuitry, digital circuitry, and/or logic circuitry, the memory and/or memory element storing the corresponding operational instructions may be embedded within, or external to, the circuitry comprising the state machine, analog circuitry, digital circuitry, and/or logic circuitry. Still further note that, the memory element may store, and the processing module, module, processing circuit, and/or processing unit executes, hard coded and/or operational instructions corresponding to at least some of the steps and/or functions illustrated in one or more of the Figures. Such a memory device or memory element can be included in an article of manufacture.

One or more embodiments have been described above with the aid of method steps illustrating the performance of specified functions and relationships thereof. The boundaries and sequence of these functional building blocks and method steps have been arbitrarily defined herein for convenience of description. Alternate boundaries and sequences can be defined so long as the specified functions and relationships are appropriately performed. Any such alternate boundaries or sequences are thus within the scope and spirit of the claims. Further, the boundaries of these functional building blocks have been arbitrarily defined for convenience of description. Alternate boundaries could be defined as long as the certain significant functions are appropriately performed. Similarly, flow diagram blocks may also have been arbitrarily defined herein to illustrate certain significant functionality.

To the extent used, the flow diagram block boundaries and sequence could have been defined otherwise and still perform the certain significant functionality. Such alternate definitions of both functional building blocks and flow diagram blocks and sequences are thus within the scope and spirit of the claims. One of average skill in the art will also recognize that the functional building blocks, and other illustrative blocks, modules and components herein, can be implemented as illustrated or by discrete components, application specific integrated circuits, processors executing appropriate software and the like or any combination thereof.

In addition, a flow diagram may include a "start" and/or "continue" indication. The "start" and "continue" indications reflect that the steps presented can optionally be incorporated in or otherwise used in conjunction with other routines. In this context, "start" indicates the beginning of the first step presented and may be preceded by other activities not specifically shown. Further, the "continue" indication reflects that the steps presented may be performed multiple times and/or may be succeeded by other activities not specifically shown. Further, while a flow diagram indicates a particular ordering of steps, other orderings are likewise possible provided that the principles of causality are maintained.

The one or more embodiments are used herein to illustrate one or more aspects, one or more features, one or more concepts, and/or one or more examples. A physical embodiment of an apparatus, an article of manufacture, a machine, and/or of a process may include one or more of the aspects, features, concepts, examples, etc. described with reference to one or more of the embodiments discussed herein. Further, from figure to figure, the embodiments may incorporate the same or similarly named functions, steps, modules, etc. that may use the same or different reference numbers and, as such, the functions, steps, modules, etc. may be the same or similar functions, steps, modules, etc. or different ones.

While the transistors in the above described figure(s) is/are shown as field effect transistors (FETs), as one of ordinary skill in the art will appreciate, the transistors may be implemented using any type of transistor structure including, but not limited to, bipolar, metal oxide semiconductor field effect transistors (MOSFET), N-well transistors, P-well transistors, enhancement mode, depletion mode, and zero voltage threshold (VT) transistors.

Unless specifically stated to the contra, signals to, from, and/or between elements in a figure of any of the figures presented herein may be analog or digital, continuous time or discrete time, and single-ended or differential. For instance, if a signal path is shown as a single-ended path, it also represents a differential signal path. Similarly, if a signal path is shown as a differential path, it also represents a single-ended signal path. While one or more particular architectures are described herein, other architectures can likewise be implemented that use one or more data buses not expressly shown, direct connectivity between elements, and/or indirect coupling between other elements as recognized by one of average skill in the art.

The term "module" is used in the description of one or more of the embodiments.

A module implements one or more functions via a device such as a processor or other processing device or other hardware that may include or operate in association with a memory that stores operational instructions. A module may operate independently and/or in conjunction with software and/or firmware. As also used herein, a module may contain one or more sub-modules, each of which may be one or more modules.

While particular combinations of various functions and features of the one or more embodiments have been expressly described herein, other combinations of these features and functions are likewise possible. The present disclosure is not limited by the particular examples disclosed herein and expressly incorporates these other combinations.

What is claimed is:

1. A wireless sensor comprises:
   a substrate;
   an antenna for receiving an inbound radio frequency (RF) signal and for transmitting an outbound RF signal;
   a sensing element for sensing a condition of an item, wherein the item or a container of the item have properties that substantially interfere with RF communication, wherein the sensing element is positioned on one end of the substrate and the antenna is positioned on an opposite end of the substrate, wherein, when the wireless sensor is mounted on the item or the container, the sensing element is proximal to the item and the antenna is at a distance from the item or the container such that the properties do not substantially interfere with the receiving of the inbound RF signal and the transmitting of the outbound RF signal;
   a transmission line on the substrate;
   a sensing integrated circuit (IC) on the substrate, wherein the sensing element is operably coupled to the antenna via the transmission line and operably coupled to the sensing element, and wherein the sensing IC is operable to:
      receive a sensed condition of the item from the sensing element;
      determine an input impedance of the wireless sensor based on the sensed condition;
      convert the input impedance into a digital value that is representative of the condition of the item; and
      output, via the antenna, the digital value or a representation of the condition of the item.

2. The wireless sensor of claim 1, wherein the substrate comprises at least one of:
   a flexible printed circuit board; and
   a printed plastic membrane.

3. The wireless sensor of claim 1, wherein the condition of the item comprises one or more:

a change in the condition with respect to a reference condition; and
a measure of the condition.

4. The wireless sensor of claim 1, wherein the condition of the item comprises one or more of:
temperature;
moisture;
pressure;
concentration level of the item; and
presence or absence detection of the item.

5. The wireless sensor of claim 1 further comprises:
a first inductor coupling the sensing IC to the sensing element; and
a second inductor coupling the sensing IC to the transmission line, wherein the first and second inductors form a transformer for impedance matching with the transmission line.

6. The wireless sensor of claim 1, wherein the sensing element comprises:
a pair of metallic traces generating a capacitance between the metal traces.

7. The wireless sensor of claim 6 further comprises:
the pair of metallic traces having a first length, a first thickness, and a first spacing; and
each of first and second traces of the transmission line have a second length, a second thickness, and a second spacing, wherein one or more of the first length, the first thickness, the first spacing, the second length, the second thickness, and the second space are selected for impedance matching with the antenna.

8. A wireless sensor comprises:
a substrate;
a dipole antenna for receiving an inbound radio frequency (RF) signal and for transmitting an outbound RF signal, wherein the dipole antenna has a first length;
a transmission line coupled to the antenna, wherein the antenna and the transmission line are on the substrate, wherein the transmission line has a second length, wherein the second length is equal to or greater than the first length;
a sensing element for generating a sensed condition of an item, wherein the sensing element is positioned on one end of the substrate and the antenna is positioned on an opposite end of the substrate;
a sensing integrated circuit (IC) on the substrate, wherein the sensing element is operable to:
receive a sensed condition of the item from the sensing element;
determine an input impedance of the wireless sensor based on the sensed condition;
convert the input impedance into a digital value that is representative of the condition of the item; and
output, via the antenna, the digital value or a representation of the condition of the item.

9. The wireless sensor of claim 8, wherein the substrate comprises at least one of:
a flexible printed circuit board; and
a printed plastic membrane.

10. The wireless sensor of claim 8, wherein the condition of the item comprises one or more:
a change in the condition with respect to a reference condition; and
a measure of the condition.

11. The wireless sensor of claim 8, wherein the condition of the item comprises one or more of:
temperature;
moisture;
pressure;
concentration level of the item; and
presence or absence detection of the item.

12. The wireless sensor of claim 8 further comprises:
a first inductor coupling the sensing IC to the sensing element; and
a second inductor coupling the sensing IC to the transmission line, wherein the first and second inductors form a transformer for impedance matching with the transmission line.

13. The wireless sensor of claim 8, wherein the sensing element comprises:
a pair of metallic traces generating a capacitance between the metal traces.

14. The wireless sensor of claim 13 further comprises:
the pair of metallic traces having a first trace length, a first thickness, and a first spacing; and
each of first and second traces of the transmission line have a second trace length, a second thickness, and a second spacing, wherein one or more of the first trace length, the first thickness, the first spacing, the second trace length, the second thickness, and the second space are selected for impedance matching with the antenna.

* * * * *